United States Patent [19]

Corbin

[11] 4,372,154
[45] Feb. 8, 1983

[54] WIRE ELONGATION TEST METHOD AND APPARATUS

[75] Inventor: Lawrence W. Corbin, Fort Wayne, Ind.

[73] Assignee: Fort Wayne Wire Die, Inc., Fort Wayne, Ind.

[21] Appl. No.: 266,600

[22] Filed: May 22, 1981

[51] Int. Cl.³ .................................................. G01N 19/00
[52] U.S. Cl. .......................................... 73/104; 73/87
[58] Field of Search .................. 73/104, 829, 826, 87; 72/274

[56] References Cited

U.S. PATENT DOCUMENTS 3,240,055  3/1966  Eddens ............................ 73/826 X
3,447,364  6/1969  Gelfand et al. ................... 73/829 X

*Primary Examiner*—Jerry W. Myracle
*Attorney, Agent, or Firm*—Gust, Irish, Jeffers & Hoffman

[57] ABSTRACT

A digital method of testing a wire drawing die to determine the percent wire elongation provided thereby in which a predetermined test length of wire is pulled through the die and then around a rotatable capstan thereby rotating the same. A train of electrical pulses is generated in response to rotational movement of the capstan, there being $10^n$ pulses generated in response to the rotational movement of the capstan caused by pulling a length of drawn wire therearound equal in length to the test length prior to drawing through the die where "n" is a positive integer greater than zero and less than five. The pulses generated during the pulling of the test length of the wire through the die are counted, and a visual indication of the pulse count with the most significant digit eliminated is provided.

12 Claims, 4 Drawing Figures

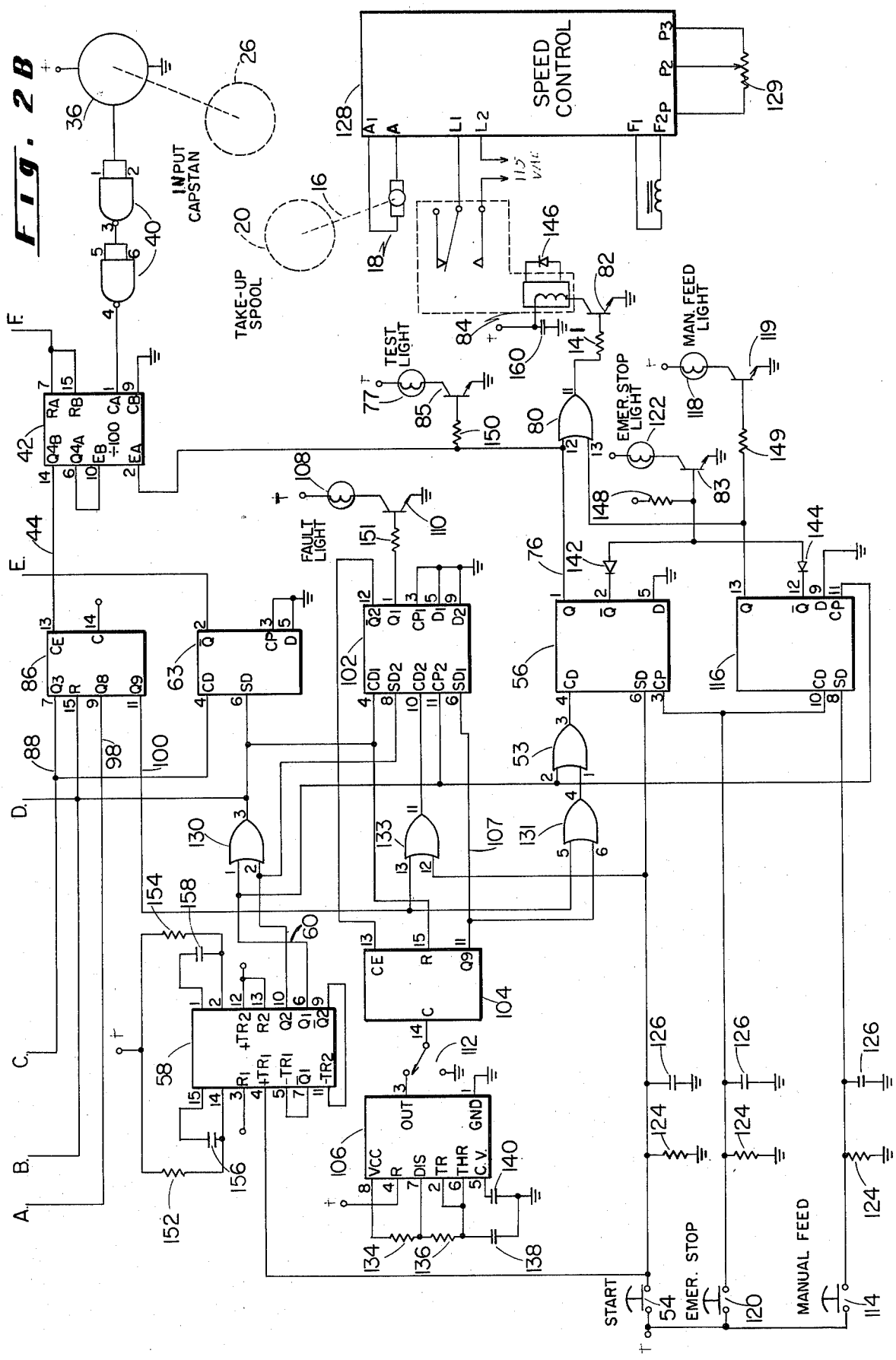

WIRE ELONGATION TEST METHOD AND APPARATUS

BACKGROUND OF THE INVENTION

1. Field of the Invention

This invention relates generally to a method and apparatus for testing a wire drawing die to determine the percent wire elongation provided thereby.

2. Description of the Prior Art

In the drawing of wire from rod stock, a succession of wire drawing dies are employed with the diameter of the wire being progressively reduced by each successive die. When the diameter of wire is reduced by drawing through a die, the length of the wire is consequently increased and in the drawing of wire through a succession of dies, it is desirable to obtain substantially the same percentage of elongation at each successive die in order to reduce the drawing force required on the wire and wear on the capstans in the drawing apparatus, and also to increase die life and drawing speed. In the past, in order to test a given wire drawing die to determine the percentage of wire elongation provided thereby, a known length of wire has been manually pulled through the die and then measured to determine the elongation from which the percentage of elongation may be calculated.

It is therefore desirable to provide a method and apparatus for automatically testing a wire drawing die which provides a direct read-out of the percentage of wire elongation provided thereby.

SUMMARY OF THE INVENTION

In accordance with the method of the invention in its broadest aspects, a predetermined test length of wire is pulled through the die and then around a rotatable capstan thereby rotating the same. A train of electrical pulses is generated in response to rotational movement of the capstan, there being $10^n$ pulses generated in response to the rotational movement of the capstan caused by pulling a length of drawn wire therearound equal in length to the test length prior to drawing through the die where "n" is a positive integer greater than zero and less than five. The pulses are counted during the pulling of the test length of wire through the die and a visual indication is provided of the pulse count with the most significant digit being eliminated.

The apparatus of the invention, in its broader aspects, comprises means for removably mounting a die to be tested, and means for measuring a predetermined test length of wire to be drawn through the die. A rotatable capstan is provided adapted to have the wire exiting from the die trained therearound, and means is provided for pulling the wire through the die and around the capstan thereby to rotate the same. Means are provided for generating a train of electrical pulses in response to rotational movement of the capstan, the pulse generating means generating $10^n$ pulses in response to rotational movement of the capstan caused by pulling a length of drawn wire therearound equal in length to the test length prior to drawing through the die where "n" is a positive integer greater than zero and less than five. Means responsive to the measuring means is provided for counting the pulses during the pulling of the test length of wire through the die, and indicating means is provided responsive to the counting means for providing a visual indication of the number of pulses counted thereby with the most significant digit eliminated.

In the preferred embodiment of the invention, the test length of wire is determined by pulling the wire around a second rotatable capstan prior to pulling the wire through the die. A second train of electrical pulses is generated in response to the rotational movement of the second capstan with a predetermined number of second pulses being generated in response to the rotational movement of the second capstan caused by pulling the test length of wire therearound. A predetermined number of the second pulses is counted and the counting of the first-named pulses is enabled during the occurrence of the predetermined number of second pulses.

It is accordingly an object of the invention to provide an improved method of testing a wire drawing die to determine the percent wire elongation provided thereby.

Another object of the invention is to provide improved apparatus for testing a wire drawing die to determine the percent wire elongation provided thereby.

A further object of the invention is to provide an improved method and apparatus for testing a wire drawing die which provides a direct read-out of the percent elongation of the wire provided thereby.

The above-mentioned and other features and objects of this invention and the manner of attaining them will become more apparent and the invention itself will be best understood by reference to the following description of an embodiment of the invention taken in conjunction with the accompanying drawings.

DESCRIPTION OF THE PREFERRED EMBODIMENT

It will be readily understood that if the length of a predetermined test length of wire before drawing is subtracted from the length of the test length of wire after drawing and the resultant elongation is divided by the test length prior to drawing, the result of the calculation is percentage elongation. From this it will be understood that if a train of pulses is generated responsive to drawing the test length of wire through a die, and from that count is deducted the number of pulses which would be generated if no elongation was provided with the resultant pulse count responsive to elongation being divided by the pulse count with no elongation, the resultant again will be the percent elongation resulting from drawing the wire through the die. Recalling now that the percent elongation resulting from drawing a predetermined length of wire through a single wire drawing die is substantially less than 100%, it will be seen that if the pulse count responsive to pulling a length of wire through the die equal in length to the test length prior to drawing is arranged to be $10^n$ where "n" is a positive integer equal to or greater than zero, dropping the most significant digit from the actual count when drawing the test length of wire through a die will result in a figure which is the percent elongation, as will be described hereafter.

Figure 1:
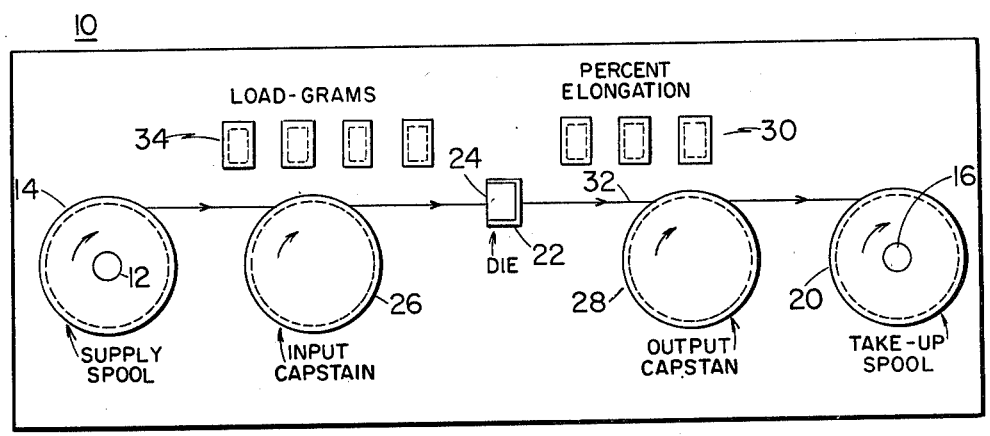
FIG. 1 is a side view of the panel of the apparatus of the invention.

Referring now to FIG. 1, the apparatus of the invention, generally indicated at 10, includes arbor 12 adapted to receive supply spool of wire 14, take-up arbor 16 driven by motor 18 (FIG. 2) and adapted to receive take-up spool 20, holder 22 for removably receiving wire drawing die 24 to be tested, rotatable input capstan 26 between die holder 22 and supply spool 14, and rotatable output capstan 28 between die holder 22 and take-up spool 20. In the preferred embodiment, input capstan 26 and output capstan 28 preferably have the same diameter. Display devices 30, such as conventional seven-segment light emiting diode display devices provide a direct read-out of the percent elongation of wire 32 drawn through die 24, and other display devices 34 provide a direct read-out of the pulling force exerted on die 24 by drawing wire 32 therethrough.

In the apparatus of the invention, motor 18 drives take-up spool 20 to pull wire 32 from supply spool 14, around input capstan 26 thereby to rotate the same, through die 24 thereby reducing the diameter of the wire with consequent elongation thereof, and around output capstan 28 thereby rotating the same.

Figure 2A:
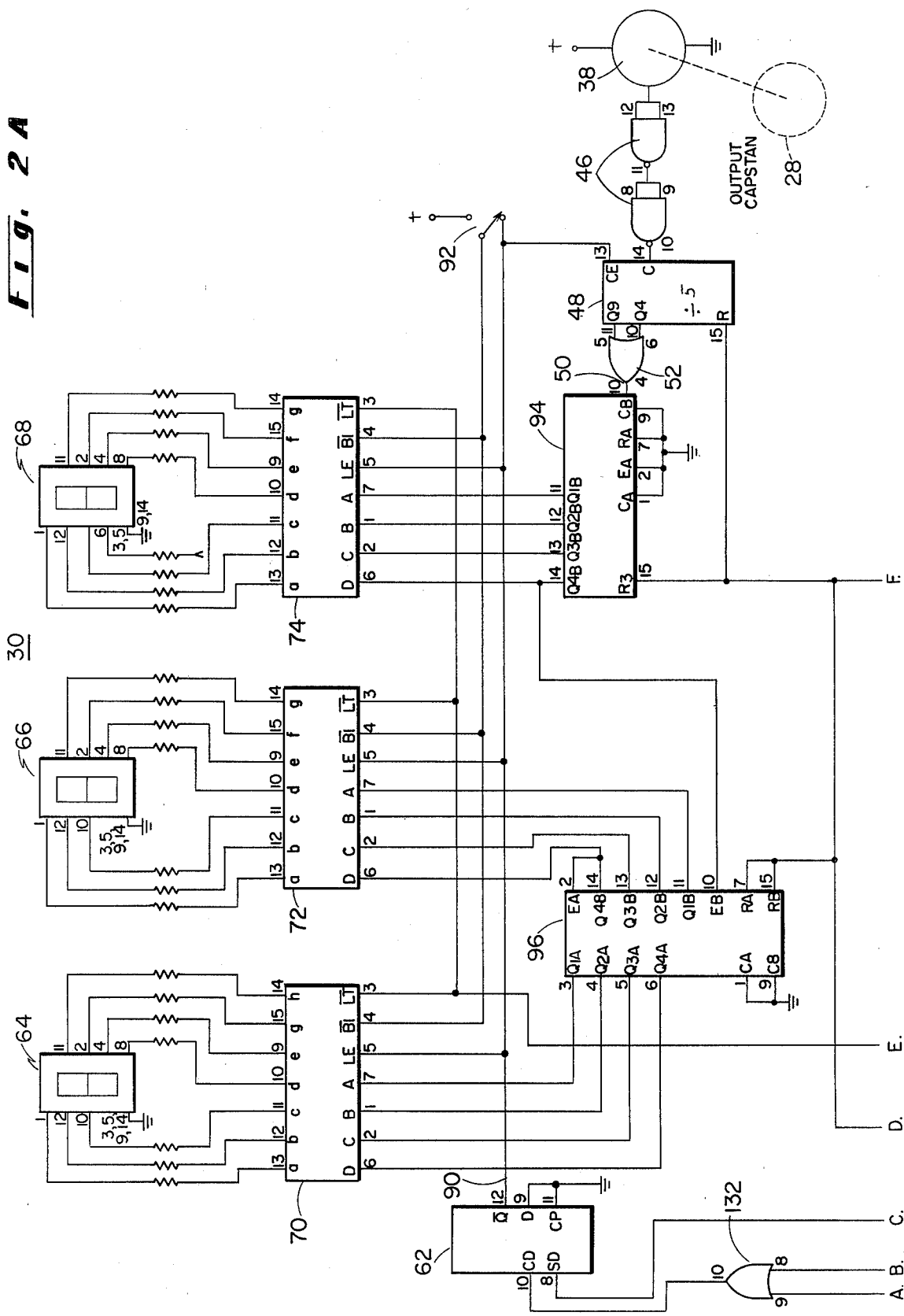
FIG. 2A and B is a schematic illustration of the apparatus of the invention.

Referring now additionally to FIG. 2 of the drawing, input capstan 26 is directly coupled to drive pulse generator 36 which, in a specific embodiment of the invention, generates 100 pulses per revolution. Output capstan 28 directly drives pulse generator 38 which, in the specific embodiment, generates 1,000 pulses per revolution. The pulses generated by pulse generator 36 are shaped by Schmidt triggers 40 and divided by 100 by counter/divider 42 to provide one pulse per revolution in output circuit 44 of divider 42. The output pulses generated by pulse generator 38 are likewise shaped by Schmidt triggers 46 and, in the specific embodiment, divided by five by decade counter/divider 48 thus providing 200 pulses per revolution in output circuit 50 of OR gate 52.

Input capstan 26 is used to determine the predetermined length of test wire and, in the illustrated embodiment, the predetermined test length is determined by five complete revolutions of input capstan 26 thus providing five pulses in output circuit 44 of dividing circuit 42. As will be hereinafter described in greater detail, the output of divider 42 is used to enable divider 48. The pulse count in output circuit 50 of divider 48 is employed to drive display devices 30, as will be hereinafter more fully described.

It will now be seen that with five complete revolutions of input capstan 26 providing five pulses in output circuit 44 of divider 42 and with divider 48 providing 200 pulses per revolution, if there was no elongation of wire 32 during drawing through die 24, output capstan 28 would also make five complete revolutions in response to pulling the test length of wire therearound for a total of 1,000 pulses. It will be seen that any counts beyond 1,000 from divider 48 in response to elongation of wire 32 as it is drawn through die 24 represent 1/1,000 of unity or 0.1% provided the elongation is less than 100%. Thus, if the most significant digit, i.e. "1" is eliminated, the remaining three digits provide a direct reading of the percentage of elongation in increments of 0.1%.

In a specific embodiment of the apparatus of the invention, actuation of momentary contact "start" switch 54 sets flip-flop 56 and also triggers one-shot multivibrator 58 to provide a single reset pulse in its output circuit 60 which resets all of the counters in the apparatus, to be hereinafter described, and sets flip-flop 63 which causes a test of LED display devices 64, 66 and 68 comprising display 30 through decode and latch circuits 70, 72 and 74 respectively.

Output circuit 76 of flip-flop 56 energizes drive motor 18 through OR gate 80, transistor 82 and relay 84. Output circuit 76 of flip-flop 56 also enables counter 42 which divides the output of pulse generator 36 by 100, as above-described. An enable pulse in output circuit 76 of flip-flop 56 also illuminates test indicator lamp 77 through transistor 85.

The output of counter/divider 42 in output circuit 44 is applied to decade counter 86. In the specific embodiment, three complete revolutions of input capstan 26 and pulse generator 36 are allowed in order to permit drive motor 18 to accelerate to full speed. After a count of three input pulses by counter 86, a pulse is provided in output circuit 88 which sets flip-flop 62. The output from flip-flop 62 in output circuit 90 blanks LED display devices 64, 66, 68 through decoder and latch circuits 70, 72, 74, respectively, and enables counter/divider 48 for output capstan 28 and output pulse generator 38. Output circuit 90 of flip-flop 62 also disables the latch in circuits 70, 72 and 74 so that data from counters 94 and 96 may be input to decoder/latch circuits 70, 72 and 74. The blanking of the display may be bypassed by switch 92 when testing for malfunction.

The output from counter/divider 48 in output circuit 50 is fed to BCD counters 94, 96 which, in turn, are coupled to LED display devices 64, 66, 68 through decoder and latch circuits 70, 72, 74, respectively, as shown. It will be understood that pulse generators 36, 38 providing fewer pulses per revolution could be employed with counter/dividers 42, 48 eliminated, however, the provision of a higher number of pulses per revolution reduces the effect of stray counts.

When decade counter 86 reaches a count of eight pulses provided by counter/divider 42, i.e. in response to five additional turns of input capstan 26 and input pulse generator 36, a pulse appears in output circuit 98 which clears flip-flop 62 which, in turn, latches the data in decoder and latch circuits 70, 72, 74 and removes the display blanking signal therefrom thereby to display the final count of the pulse output of counter/divider 48 with the most significant digit, i.e. one, eliminated, as above described.

It will be seen that in the illustrated embodiment, the pulse count from output generator 38 and counter/divider 48 is 1,000 pulses in response to pulling the test length of wire through the die but, with no elongation, or $10^n$ where "n" equals 3. From a practical standpoint, "n" must be greater than zero and less than five, and preferably two or three in order to provide meaningful results.

Following the test period, input capstan 26 and input pulse generator 36 make one additional turn which provides an output pulse in output circuit 100 of decade counter 86 which resets flip-flop 56 to deenergize motor 18 and disable counter/divider 42.

The output pulse from one-shot multivibrator 58 initiated by actuation of start switch 54 also sets flip-flop 102 which enables counter 104 which counts the output pulses from free-running oscillator 106. In the event that the test wire 32 breaks or for any other reason the test is not completed in a predetermined time, about nine cycles of the output of oscillator 106 or approximately 80 seconds, the output of counter 104 in output circuit 107 sets flip-flop 102 to energize fault indicator light 108 through transistor 110. The output of counter 104 also resets flip-flop 56 to deenergize drive motor 18. Switch 112 removes oscillator 106 from counter 104 thus bypassing the fault cycle circuit.

Actuation of manual feed switch 114 sets flip-flop 116 thereby to actuate relay 84 to energize drive motor 18 and to energize manual feed indicator lamp 118 through transistor 119. Actuation of stop switch 120 resets flip-flops 56, 116 to terminate the test cycle at any time and also to illuminate emergency stop indicator lamp 122 through transistor 83.

It will be observed that with "n" equal to three, the percentage elongation is displayed to an accuracy of one-tenth of one percent. With "n" equaling two, the percent elongation is displayed to an accuracy of one percent whereas, with "n" equalling four, the percent elongation is displayed with an accuracy of one-hundredth of a percent.

In a physical embodiment of the system schematically shown in FIG. 2, the following components and component values were employed:

| | |
|---|---|
| Pulse generator 36 | DRC Corp., 152-010-100-18U |
| Pulse generator 38 | DRC Corp., 152-010-1000-18U |
| Schmidt triggers 40, 46 | 4093 |
| Counters 42, 94, 96 | 4518 |
| Decade Counters 48, 86, 104 | 4017 |
| OR Gates 52, 53, 80, 130, 131, 132, 133 | 4071 |
| Flip-flops 56, 62, 63, 102, 116 | 4013 |
| Transistors 82, 83, 85, 110, 119 | ECG 123a |
| Multivibrator 58 | 4098 |
| Decoder/latches 70, 72, 74 | 4511 |
| Oscillator 106 | 555 |
| Resistors 124 | 33K |
| Capacitors 126, 160 | .1 uf |
| Motor speed control 128 | NOVA, B & B Motors, SH102 |
| Potentiometer 129 | 1K |
| Resistors 134, 136 | 2.2M |
| Capacitor 138 | 2 uf |
| Capacitor 140 | .01 uf |
| Diodes 142, 144, 146 | IN4001 |
| Resistors 141, 148, 149, 150, 151 | 3K |
| Resistors 152, 154 | 470K |
| Capacitors 156, 158 | .22 uf |

Figure 3:
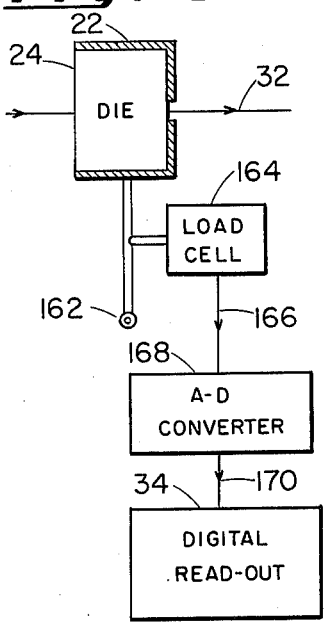
FIG. 3 shows in block diagram form the die pull testing system used with the apparatus of the invention.

Referring now to FIG. 3, it is desirable also to provide in test apparatus 10 a system fro providing a direct read-out of the pulling force exerted on die 24 by the drawing of wire 32 therethrough. To that end, fixture 22 in which die 24 is removably mounted is pivotally mounted, as at 162 and bears on conventional load cell 164. Output circuit 166 from load cell 164 is coupled to analog-to-digital converter 168 which has its output 170 coupled to display devices 34.

While there have been described above the principles of this invention in connection with specific apparatus, it is to be clearly understood that this description is made only by way of example and not as a limitation of the scope of the invention.

What is claimed is:

1. A digital method of testing a wire drawing die to determine the percent wire elongation provided thereby when the elongation is less than 100% comprising the steps of: pulling a predetermined test length of wire through the die and then around a rotatable capstan thereby rotating the same, generating a train of electrical pulses in response to rotational movement of said capstan, there being $10^n$ pulses generated in response to the rotational movement of said capstan caused by pulling a length of drawn wire therearound equal in length to said test length where "n" is a positive integer greater than zero and less than five; counting said pulses during the pulling of said test length of wire through the die; and providing a visual indication of the pulse count with the most significant digit eliminated.

2. The method of claim 1 wherein said test length of wire is determined by pulling the wire around a second rotatable capstan prior to pulling the wire through the die, generating a second train of electrical pulses in response to rotational movement of said second capstan caused by pulling said test length of wire therearound; counting a predetermined number of second pulses; and enabling said first-named pulse counting during the occurance of said predetermined number of second pulses.

3. The method of claim 2 wherein said enabling step is initiated following generation of a second predetermined number of said second pulses.

4. The method of claim 2 wherein "n" equals three.

5. The method of claim 4 wherein said capstans are of equal diameter, there being 200 of said first-named pulses generated in response to each revolution of said first-named capstan and there being one of said second pulses generated in response to each revolution of said second capstan.

6. Apparatus for digitally testing a wire drawing die to determine the percent wire elongation provided thereby when the elongation is less than 100% comprising: means for removably mounting a die to be tested; means for measuring a predetermined test length of wire to be drawn through the die; a rotatable capstan adapted to have the wire exiting from the die trained therearound; means for pulling wire through the die and around said capstan thereby to rotate the same; means for generating a train of electrical pulses in response to rotational movement of said capstan, said pulse generating means generating $10^n$ pulses in response to rotational movement of said capstan caused by pulling a length of drawn wire therearound equal in length to said test length where "n" is a positive integer greater than zero and less than five; means responsive to said measuring means for counting said pulses during the pulling of said test length of wire through the die; and indicating means responsive to said counting means for providing a visual indication of the number of pulses counted thereby with the most significant digit eliminated.

7. The apparatus of claim 6 wherein said measuring means comprises a second rotatable capstan adapted to have the wire entering the die trained therearound thereby to rotate the same, means for generating a second train of pulses in response to rotational movement of said second capstan; means for counting a predetermined number of said second pulses; and means coupling said second pulse counting means to said first-named counting means for enabling the same during the occurrence of said predetermined number of said second pulses.

8. The apparatus of claim 7 wherein said second pulse counting means is adapted to generate another predetermined number of second pulses prior to generation of said first-named predetermined number of second pulses.

9. The apparatus of claim 8 wherein said second pulse counting means is adapted to provide a first signal following said other predetermined number of pulses for enabling said first pulse counting means and a second signal following said first-named predetermined number of second pulses for disabling said first pulse counting means.

10. The apparatus of claim 9 wherein each of said first and second pulse generating means comprises means coupled to the respective capstan and driven thereby to generate signals having a repetition rate which is a multiple of the repetition rate of the respective pulse train, and dividing means coupled to the respective signal generating means for dividing the output thereof by the respective multiple to provide the respective pulse train.

11. The apparatus of claim 7 wherein "n" equals three.

12. The apparatus of claim 11 wherein said capstans are of equal diameter, said first pulse generating means generating 200 of said first-named pulses in response to each revolution of said first-named capstan, said second pulse generating means generating one of said second pulses in response to each revolution of said second capstan.

* * * * *